(12) United States Patent
Hiruma et al.

(10) Patent No.: US 8,003,083 B2
(45) Date of Patent: Aug. 23, 2011

(54) BENZYLIDENE MALONAMIDE AND SALT THEREOF, ULTRAVIOLET RAY ABSORBENT, AND AGENT FOR EXTERNAL APPLICATION TO THE SKIN

(75) Inventors: Takuya Hiruma, Yokohama (JP); Masaru Suetsugu, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 310 days.

(21) Appl. No.: 12/302,022

(22) PCT Filed: Jun. 11, 2007

(86) PCT No.: PCT/JP2007/000619
§ 371 (c)(1),
(2), (4) Date: Nov. 22, 2008

(87) PCT Pub. No.: WO2007/144981
PCT Pub. Date: Dec. 21, 2007

(65) Prior Publication Data
US 2010/0254921 A1      Oct. 7, 2010

(30) Foreign Application Priority Data
Jun. 16, 2006   (JP) ................ 2006-166866

(51) Int. Cl.
*A61K 7/42* (2006.01)
*A61K 7/06* (2006.01)
*A61K 9/00* (2006.01)
*C07C 303/00* (2006.01)
*C07C 229/00* (2006.01)
*C07C 233/00* (2006.01)

(52) U.S. Cl. ......... 424/59; 424/70.9; 424/400; 564/155; 560/12; 560/37

(58) Field of Classification Search ............ 424/59, 424/70.9, 400; 564/155; 560/12, 37
See application file for complete search history.

(56) References Cited

U.S. PATENT DOCUMENTS

| 5,021,478 | A | 6/1991 | Ravichandran et al. |
| 5,087,729 | A * | 2/1992 | Matsuno et al. ............ 560/41 |
| 6,090,374 | A | 7/2000 | Habeck et al. |
| 2001/0031866 | A1* | 10/2001 | Gupta et al. .............. 544/215 |
| 2006/0018848 | A1* | 1/2006 | Richard .................... 424/59 |

FOREIGN PATENT DOCUMENTS

| EP | 1591099 A2 | 11/2005 |
| JP | 07330680 | 12/1995 |
| WO | 2004-020398 A1 | 3/2004 |
| WO | WO 2004-020398 A1 | 3/2004 |

OTHER PUBLICATIONS

International Preliminary Report on Patentability issued in corresponding International Application PCT/JP2007/000619, 2007.
Extended European Search Report issued on Dec. 23, 2010, in corresponding European Patent Application EP 07 73 7274.

\* cited by examiner

*Primary Examiner* — Mina Haghighatian
(74) *Attorney, Agent, or Firm* — Townsend & Banta

(57) ABSTRACT

The present invention is benzilidene malonamide represented by the following formula (1) and salts thereof, an ultraviolet absorbent consisting of said new compound, and an external preparation containing this ultraviolet absorbent.

The object of the present invention is to provide a new ultraviolet absorbent that is highly soluble in water, has superior absorption capacity over a wide ultraviolet wavelength range, has no absorption in the visible region, and is also highly stable and safe.

(1)

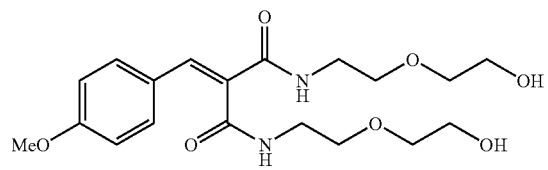

4 Claims, 1 Drawing Sheet

[FIG. 1]
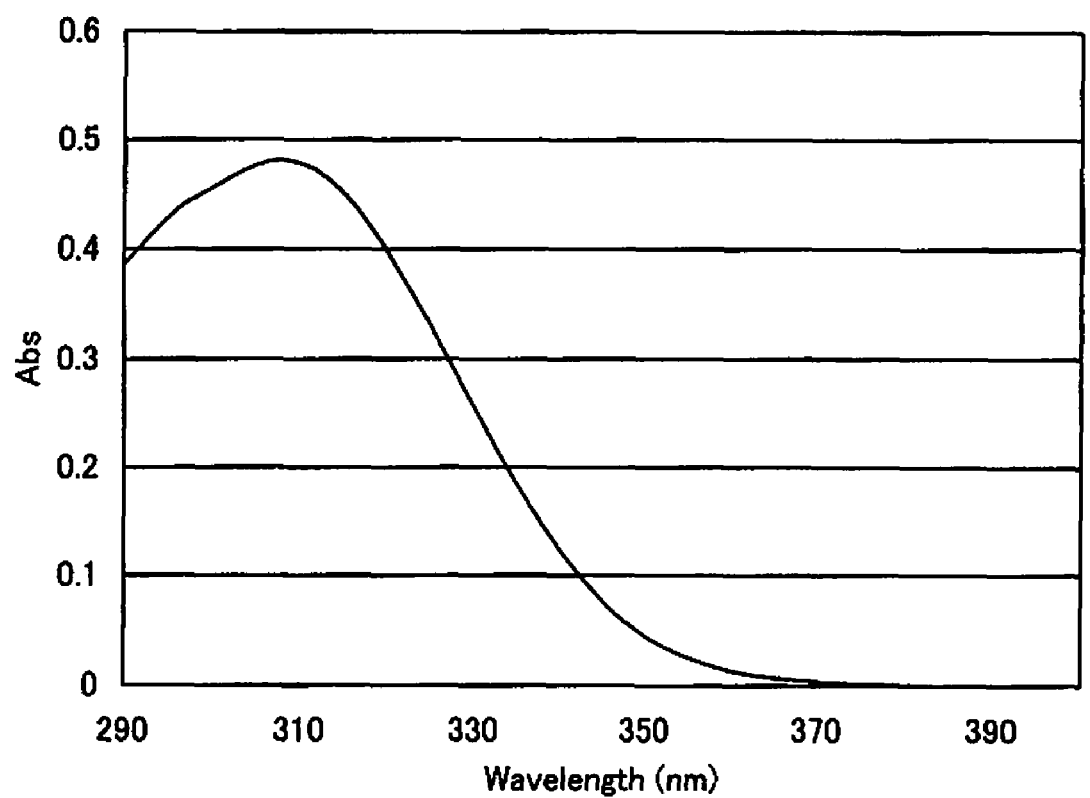

BENZYLIDENE MALONAMIDE AND SALT THEREOF, ULTRAVIOLET RAY ABSORBENT, AND AGENT FOR EXTERNAL APPLICATION TO THE SKIN

TECHNICAL FIELD

The present invention relates to novel benzilidene malonamide and its salt. The present invention specifically relates to its use as an ultraviolet absorbent that is highly water soluble and does not absorb the visible light region, as well as an ultraviolet absorbing composition, particularly an external preparation, that contains it.

BACKGROUND ART

Among ultraviolet light contained in sunlight, the ultraviolet light having a wavelength of 290 nm or less is absorbed by the ozone layer and therefore does not reach the earth surface, but the ultraviolet light of 290 nm to 400 nm reaches the earth surface and has various effects. From the dermatological point of view, it is known that the intermediate wavelength ultraviolet light of 290-320 nm causes the formation of erythema and blisters, acceleration of melanin formation, pigmentation, etc. The long wavelength ultraviolet light of 320-400 nm has the instant effect of darkening the skin immediately after irradiation, and, since its energy reaches the corium, it is said to affect the elastic fibers in the blood vessel walls and the connective tissues. Of these, the intermediate-long wavelength ultraviolet light accelerates aging of the skin and is believed to be a cause of pigmented spots, freckles, wrinkles, etc.

In order to protect the skin from such ultraviolet light, ultraviolet absorbents such as benzotriazole derivatives, benzophenone derivatives, salicylic acid derivatives, paraminobenzoic acid derivatives, cinnamic acid derivatives, and urocanic acid derivatives have been used.

However, these ultraviolet absorbents are generally oil soluble and could not be added to water based products. Recently ultraviolet protection is deemed important not only for bathing in summer and ski areas in winter but also in daily life, and therefore the ultraviolet protection effect is desired even for common skin care cosmetics. Therefore, development of a water soluble ultraviolet absorbent that can be added in a sufficient amount to water based skin care cosmetics is desired.

However, there have been very few water soluble ultraviolet absorbents; sodium 2-hydroxy-4-methoxy-5-sulfoxonium benzophenone is known to be currently used. However, since this substance is a sulfonate, it affects the pH of the formula system and the pH of the formula system affects the ultraviolet absorption region, which is problematic. Also, although this substance is water soluble its solubility is merely approximately 6% at 25° C. and there is a problem in that a high blend ratio in a product leads to precipitation at lower temperatures. Furthermore, this substance also has absorption in the visible light region and thus has a light yellow color and therefore affects the color tone of the product, which is a shortcoming.

Patent Document 1 discloses a p-aminobenzamide derivative having a 2-deoxyhexose residue and Patent Document 2 discloses a cinnamide having a 2-deoxyhexose residue; however, their water solubility is low and insufficient and therefore they are not necessarily satisfactory.

On the other hand, ultraviolet absorbents are used also in areas other than pharmaceuticals and cosmetics; for example, they are added to various materials such as paints, dyes, pigments, various resins, synthetic rubber, films, and fibers for the purpose of adding ultraviolet light absorption capacity to protect the product itself or products coated by the paint or film from ultraviolet light and thus prevent degradation, degeneration and such to maintain the product quality. However, conventional ultraviolet absorbents have a problem in that they are sublimed due to heating during paint baking and/or resin molding, or, even without heating, they are sublimed gradually as time goes on and their effect decreases.

Also, when adding an ultraviolet absorbent to an external preparation, it has to be a compound that does not irritate the skin and is highly safe. It is also important that the compound itself be stable, i.e. not decomposed by exposure to sunlight.

Patent Citation 1: Japanese Patent Laid-Open H10-120698 bulletin

Patent Citation 2: Japanese Patent Laid-Open 2002-363195 bulletin

DISCLOSURE OF INVENTION

Technical Problem

The present invention was carried out in view of the problems mentioned above; its object is to provide a new chemical compound that has a high water solubility, superior absorption capacity over a wide range of the ultraviolet wavelength region, no absorption in the visible region, and high stability and safety, and to use it as an ultraviolet absorbent.

Technical Solution

That is, the present invention provides benzilidene malonamide represented by the following general formula (1) and salts thereof.

[Chemical formula 1]

(1)

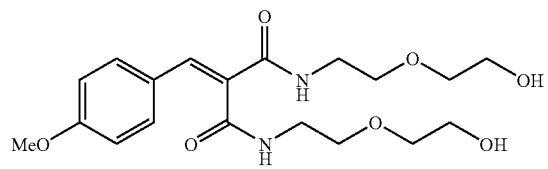

Also, the present invention provides an ultraviolet absorbent comprising benzilidene malonamide of the aforementioned formula (1) or a salt thereof.

Furthermore, the present invention provides an ultraviolet absorbing composition comprising benzilidene malonamide of the aforementioned formula (1) or a salt thereof.

Furthermore, the present invention provides an external preparation comprising benzilidene malonamide of the aforementioned formula (1) or a salt thereof.

Furthermore, the present invention provides the aforementioned external preparation that additionally contains inorganic powder.

Advantageous Effects

Benzilidene malonamide of the present invention is highly water soluble and can be blended in water based products.

It also has exceptional ultraviolet light absorption capacity over a wide region of the ultraviolet wavelengths and is useful as a highly safe and stable ultraviolet absorbent.

Therefore, by blending it in, an ultraviolet absorbing composition and/or external preparation having a high ultraviolet prevention effect as well as superior safety and stability can be obtained.

Furthermore, since benzilidene malonamide of the present invention does not have absorbance in the visible region, there is no problem of coloring of products.

BRIEF DESCRIPTION OF DRAWINGS

FIG. 1 is an ultraviolet absorption spectrum of the benzilidene malonamide of formula (1).

BEST MODE FOR CARRYING OUT THE INVENTION

The new compound of the present invention is benzilidene malonamide represented by the following formula (1) and its chemical name is bis-N,N'-[2-(2-hydroxyethoxy)ethyl]-4-methoxybenzilidene malonamide.

[Chemical formula 2]

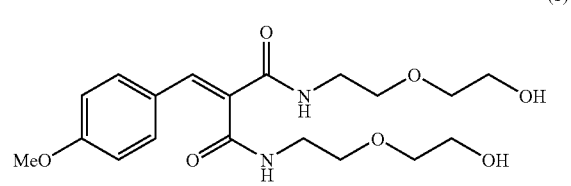

(1)

A representative method for preparing the new compound of the present invention is shown below.

Preparation Method 1

(In this formula, $R_1$ denotes an alkyl, aryl, arylalkyl, and such.)

That is, the compound of formula (2) can be easily synthesized by means of a prior art condensation reaction between p-methoxybenzaldehyde (p-anisaldehyde) and a malon ester. For the reaction solvent, toluene, benzene, pyridine and such, and for the catalyst, piperidine, acetic acid, ammonium acetate and such can be used independently or in combination. These two can be refluxed in the reaction solvent to synthesize the compound of formula (2). Next, the benzilidene malonamide of formula (1) can be synthesized by reacting, under heated conditions, 2-(2-aminoethoxy)ethanol with the compound of formula (2) thus produced.

It can also be synthesized easily by hydrolyzing the compound of formula (2) to obtain the dicarboxylic acid of formula (3) and using a prior art amide bond formation method with 2-(2-aminoethoxy)ethanol. That is, the benzilidene malonamide of the formula (1) can be synthesized by activating the carboxyl group to obtain the activated form and reacting 2-(2-aminoethoxy)ethanol with the activated form.

For activating carboxyl groups, methods such as the following (1)-(3) can be used.

(1) The activated ester method using p-nitrophenyl ester, N-hydroxysuccinimide ester, etc.

(2) The mixed acid anhydrate method using a mixed acid anhydrate with carboxylic monoalkyl ester using isobutyloxycarbonyl chloride, ethyloxycarbonyl chloride, etc.

(3) The acid chloride method using an acid chloride obtained by a reaction with phosphorus trichloride, phosphorus pentachloride, thionyl chloride, etc.

Furthermore, the benzilidene malonamide of formula (1) can also be synthesized by adding a coupling reagent to a mixed solution of the dicarboxylic acid of formula (3) and 2-(2-aminoethoxy)ethanol to initiate coupling. For the coupling reagent, N,N'-dicyclohexylcarbodiimide (DCC), N-hydroxysuccinimide, 1-hydroxybenzotriazole and DCC and such can be used.

It can also be prepared by using the preparation method shown below.

[Chemical formula 3]

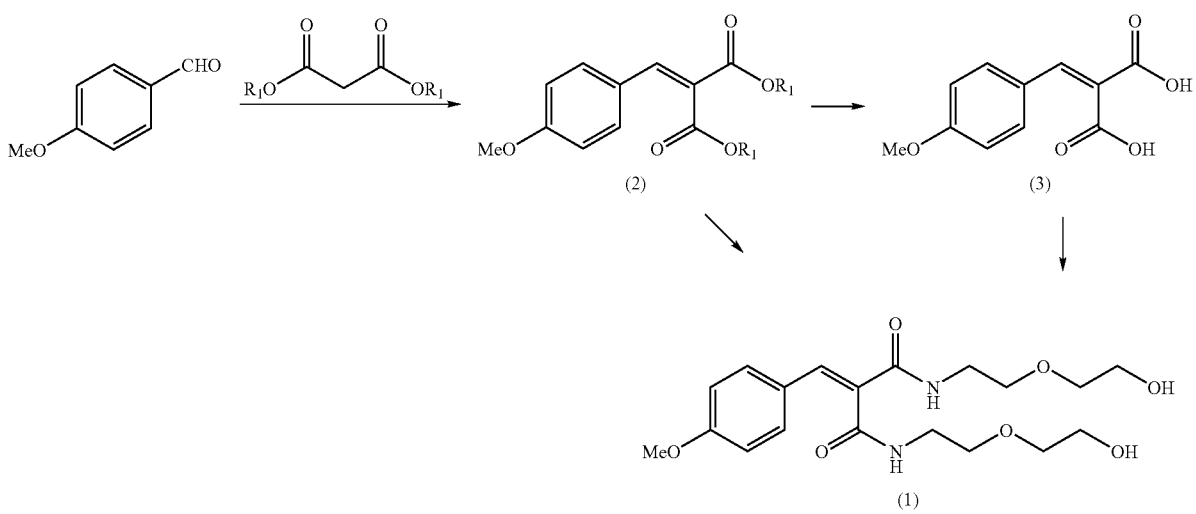

Preparation Method 2

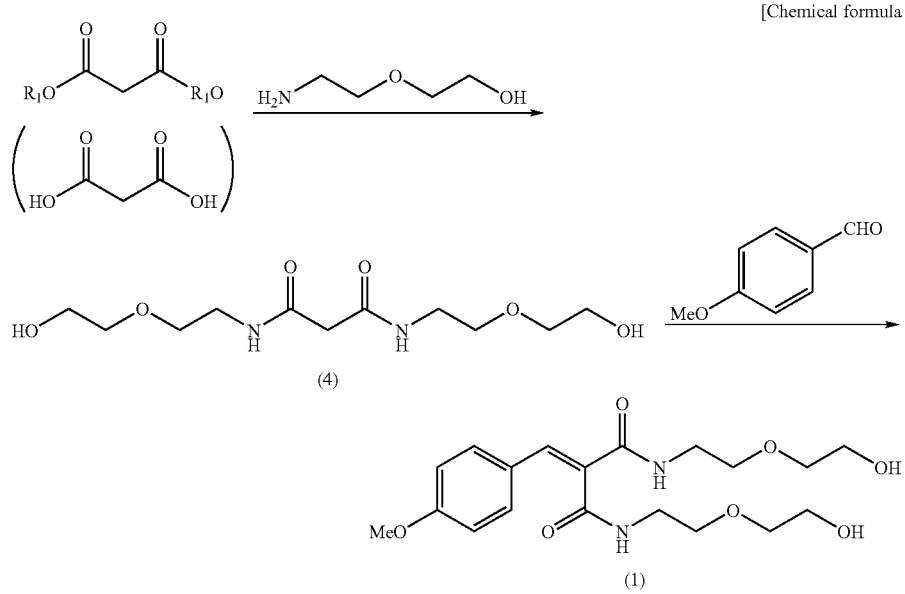

[Chemical formula 4]

That is, the diamide of formula (4) can easily be synthesized by reacting a malonic ester and 2-(2-aminoethoxy)ethanol. Also, it is possible to easily synthesize the diamide of formula (4) by using a prior art amide bond formation method on malonic acid and 2-(2-aminoethoxy)ethanol.

And, the benzilidene malonamide of formula (1) can be synthesized by means of a prior art condensation reaction between the diamide of formula (4) and p-methoxybenzaldehyde (p-anisaldehyde).

The compounds required for the preparation methods described above can be commercially obtained from Tokyo Chemical Industry Co., Ltd., Wako Pure Chemical Industries, ltd., Aldrich Co. Ltd., etc.

The benzilidene malonamide of the present invention can be turned into an inorganic salt or organic salt by means of applicable methods. Selection of this salt is not limited in particular; examples of the inorganic salt include chlorides, sulfates, phosphates, hydrobromide, sodium salts, potassium salts, magnesium salts, calcium salts, and ammonium salts. Examples of the organic salt include acetates, lactates, maleates, fumarates, tartrates, citrates, methanesulfonate, p-toluenesulfonates, triethanolamine salts, diethanolamine salts, and amino acid salts.

The benzilidene malonamide and the salt thereof are useful as an ultraviolet absorbent; it can be mixed with various substances to constitute an ultraviolet absorbing composition. The ultraviolet absorbent and ultraviolet absorbing composition of the present invention can be blended into various products to which ultraviolet absorbents are to be added. It is particularly preferable to blend them into external preparations.

An external preparation containing the ultraviolet absorbent of the present invention manifests a superior ultraviolet prevention effect; also, since this ultraviolet absorbent does not decompose even with exposure to the sunlight, its effect is manifested for a long time in a stable manner. Also, it does not absorb the visible light and therefore there is no coloring of the products. Furthermore, it does not cause skin troubles either and is very useful as an external preparation for sunscreening.

In order to increase the ultraviolet shielding effect of a sunscreen external preparation, it is desirable to use not only organic compound ultraviolet absorbents but also inorganic powder ultraviolet shielding agents. Also, inorganic powder is often blended into makeup cosmetics as well. However, using both an organic ultraviolet absorbent and an inorganic powder sometimes causes discoloration.

The ultraviolet absorbent of the present invention does not cause discoloration even when it is blended into an external preparation along with inorganic powder, and therefore it can be used simultaneously with inorganic powders.

The selection of the inorganic powder used in the present invention is not limited as long as the selection comes from those commonly used in cosmetics and/or medicinal drugs. Examples include inorganic powders such as talc, kaolin, boron nitride, mica, sericite, biotite, muscovite, phlogopite, synthetic mica, synthetic mica, vermiculite, magnesium carbonate, calcium carbonate, silicic anhydrate, aluminum silicate, aluminum oxide, barium silicate, calcium silicate, magnesium silicate, tungstic acid metal salt, magnesium, silica, zeolite, barium sulfate, firing calcium sulfate calcined gypsum, calcium phosphate, fluorine-apatite, hydroxyapatite, ceramic powder, and metallic soaps (for example, zinc myristate, calcium palmitate, and aluminum stearate), and inorganic pigments such as titanium dioxide, zinc oxide, iron oxide, iron titanate, carbon, lower titanium oxide, mango violet, cobalt violet, chromium oxide, chromium hydroxide, cobalt titanate, ultramarine blue and Berlin blue, titanium oxide-coated mica, titanium oxide-coated bismuth oxychloride, titanium oxide-coated talc, colored titanium oxide-coated mica, bismuth oxychloride, and fish scale flakes.

For sunscreen external preparations such as sunscreen cosmetics in particular, fine particle titanium oxide, fine particle zinc oxide and such are preferably used.

When blending the ultraviolet absorbent of the present invention into an external preparation, the blend ratio is not limited and can be determined based on the desired ultraviolet absorption capacity. Usually, it is 0.001-20 wt %, preferably 0.01-10 wt %, of the total amount of the external preparation.

The blend ratio of the inorganic powder is not limited either. It is determined as appropriate for the external preparation product; usually, it is blended in to be 0.1-99.5 wt % of the total amount of the external preparation.

The product form of the external preparation of the present invention is not limited in particular. Examples include skin-care cosmetics such as lotions, emulsions, creams, essences and self tanning agents, as well as makeup cosmetics such as foundation cosmetics, foundations, lipsticks, face colors, and eyeliners, and cosmetics for head hair and/or head skin such as hair sprays, hair tonics, and hair liquids.

In addition to the aforementioned essential ingredients, other ingredients used in cosmetics and medicinal drugs can be blended as necessary in the external preparation of the present invention; examples of such ingredients include liquid fats and oils, solid fats and oils, waxes, hydrocarbons, higher fatty acids, higher alcohols, esters, silicones, anionic surfactants, cationic surfactants, ampholytic surfactants, nonionic surfactants, humectants, water-soluble polymers, thickeners, coating agents, sequestering agents, lower alcohols, polyhydric alcohols, sugars, amino acids, organic amines, pH adjusting agents, skin nutrients, vitamins, antioxidants, perfumes, powders, coloring agents, and water; they can be blended in as necessary and appropriate. Ultraviolet absorbents other than benzilidene malonamide and its salt can also be blended into the external preparation of the present invention.

Also, the ultraviolet absorbent of the present invention can be blended into products other than external preparations such as paints, dyes, pigments, various resins, synthetic rubber, latex, film, fiber, etc. for protection against ultraviolet light. When blending the ultraviolet absorbent of the present invention into various products, it is also possible to first prepare an ultraviolet absorbing composition by mixing it with other raw material compounds or by preparing an aqueous solution, and then blending this in.

The ultraviolet absorbent of the present invention has superior heat stability and does not sublimate, and therefore its efficacy can be maintained for a long time. The blend ratio in various products and ultraviolet absorbing compositions is usually 0.001-20 wt %, preferably 0.01-10 wt %.

EXAMPLES

The present invention is described in detail below by referring to Examples. The present invention is not limited to these.

Example 1

Synthesis of Benzilidene Malonamide (1) (bis-N,N'-[2-(2-hydroxyethoxy)ethyl]-4-methoxybenzilidene malonamide)

Diethyl malonate (0.72 mL, 4.76 mmol) and 2-(2-aminoethoxy)ethanol (1.00 g, 9.51 mmol) were stirred at 130° C. for 3 hours. After the temperature naturally cooled down to room temperature, toluene (6 mL) was added to what remained, to which p-methoxybenzaldehyde (0.65 g, 4.76 mmol) and piperidine (0.19 mL, 1.90 mmol) were added. The reaction solution was refluxed for 6 hours and the temperature was cooled down naturally. The residual obtained after concentration was purified with silica gel column chromatography (chloroform/methanol=30/1) to obtain the benzilidene malonamide of formula (1) (1.11 g, yield 59%).

The obtained compound was identified with a 1H-NMR (ECP400 from JE0L). Tetramethylsilane was used as the internal standard. The chemical analysis values are as follows:

$^1$H-NMR (DMSO-$d_6$, TMS, ppm)

δ 8.37 (t, J=5.3 Hz, 7.49 (t, J=5.3 Hz, 1H), 7.45 (d, J=8.7 Hz, 2H), 7.31 (s, 1H), 6.94 (d, J=8.7 Hz, 2H), 4.51 (t, J=5.3 Hz, 1H), 4.47 (t, J=5.3 Hz, 1H), 3.78 (s, 3H), 3.52-3.40 (m, 12H), 3.36-3.31 (m, 4H).

Test example 1

Absorbance Measurement

An ultraviolet absorption spectrum of the benzilidene malonamide obtained in Example 1 was measured (solvent: water, concentration 10 ppm, optical path length 1 cm) by using a spectrophotometer (V-560 from Jasco Co. Ltd.). The results are shown in FIG. 1. As clearly shown in FIG. 1, the benzilidene malonamide of the present invention had superior absorption capacity over a wide ultraviolet wavelength region.

Test Example 2

Absorbance Measurement 405 nm visible light absorbance of the benzilidene malonamide obtained in Example 1 was measured (solvent: water, optical path length 1 cm) by using a spectrophotometer (V-560 from Jasco Co. Ltd.). For a Comparative example, sodium 2-hydroxy-4-methoxy-5-sulfoquisonium benzophenone, a conventional water soluble ultraviolet absorbent, was measured in the same manner. The results are shown in Table 1.

TABLE 1

| Ultraviolet absorbent | Concentration (wt %) | Absorbance |
|---|---|---|
| Benzilidene malonamide of formula (1) | 10 | 0 |
| Sodium 2-hydroxy-4-methoxy-5-sulfoxonium benzophenone | 6 | 1.99 |
| | 1 | 0.32 |
| | 0.1 | 0.06 |

As clearly shown in Table 1, the benzilidene malonamide of the present invention does not absorb the visible region whose wavelength is longer than 400 nm. Therefore the crystals were white and the aqueous solution was colorless and clear.

On the other hand, the Comparative compound has absorbance in the visible region and the crystals are light yellow and the aqueous solution is yellow; the blend ratio is therefore limited due to the coloring and it cannot exhibit sufficient ultraviolet absorbing effects.

Test Example 3

Solubility in Water

Solubility in water was measured for the benzilidene malonamide of the present invention. For a Comparative example, sodium 2-hydroxy-4-methoxy-5-sulfoquisonium benzophenone was measured in the same manner. The results are shown in Table 2.

TABLE 2

| Ultraviolet absorbent | Solubility (room temperature) [wt %] |
|---|---|
| Benzilidene malonamide of formula (1) | 30 or more |
| Sodium 2-hydroxy-4-methoxy-5-sulfoxonium benzophenone | 6 |

As clearly shown in Table 2, the benzilidene malonamide of the present invention has very high solubility in water and can be blended in at a high concentration. On the other hand, the water soluble ultraviolet absorbent of the Comparative example has low solubility in water and a high blend ratio is hard to achieve; when the blend ratio is high it may precipitate during low temperature storage. Therefore, its use is limited from the point of view of product stability as well.

Test Example 4

Ultraviolet Prevention Effect

<Test Method>
An actual use test was conducted on a beach in summer. The same amount of sample was applied on the left and right halves of panelists' backs. The degree of sunburn after exposure to direct sunlight was evaluated based on the following criteria. The test was conducted with a group of 10 panelists.
(Assessment Criteria)
Very effective: No or very little sunburn symptoms were observed.
Effective: A mild degree of sunburn symptoms were observed.
Not effective: A strong degree of sunburn symptoms were observed.
(Evaluation)
⊚: 80% or more of the subjects report "very effective" or "effective."
○: 50% or more and less than 80% of the subjects report "very effective" or "effective."
∇: 30% or more and less than 50% of the subjects report "very effective" or "effective."
X: Less than 30% of the subjects report "very effective" or "effective."

Preparation of the Samples (a) lotion and (b) cream were prepared according to the following recipes. For the ultraviolet absorbent, benzilidene malonamide (bis-N,N'-[2-(2-hydroxyethoxy)ethyl]-4-methoxybenzilidene malonamide) of the present invention and, as a Comparison example, a water soluble ultraviolet absorbent sodium 2-hydroxy-4-methoxy-5-sulfoquisonium benzophenone were used.

"(a) Lotion"

| (Alcohol phase) | |
|---|---|
| 95% ethanol | 25.0 mass % |
| POE(25) hydrogenated castor oil | 2.0 |
| Preservative | Appropriate amount |
| Perfume | Appropriate amount |
| (Water phase) | |
| Ultraviolet absorbent | 1-10 |
| Glycerin | 5.0 |
| Sodium hexametaphosphate | Appropriate amount |
| Ion-exchanged water | Balance |

(Preparation Method)
The water phase and the alcohol phase were separately prepared and then mixed together.

"(b) Cream"

| Stearyl alcohol | 7.0 wt % |
|---|---|
| Stearic acid | 2 |
| Hydrogenated lanolin | 2.0 |
| Squalane | 5.0 |
| 2-octyldodecyl alcohol | 6.0 |
| POE(25) cetyl ether | 3.0 |
| Glycerin monostearate | 2.0 |
| Propylene glycol | 5.0 |
| Ultraviolet absorbent | 1-10 |
| Perfume | Appropriate amount |
| Sodium hydrogen sulfite | 0.03 |
| Ethylparaben | 0.3 |
| Ion-exchanged water | Balance |

(Preparation Method)
Propylene glycol and the ultraviolet absorbent were dissolved in ion-exchanged water and the temperature was raised to 70° C. and maintained. The other ingredients were mixed, heated and melted, and the temperature was maintained at 70° C. (oil phase). The oil phase was added to the water phase and pre-emulsification was conducted; after a homomixer was used to emulsify the mixture homogeneously, the temperature was cooled down to 30° C. while thorough stirring was maintained.
<Results>
The results are shown in Table 3.

TABLE 3

(a) Lotion

| Ultraviolet absorbent | Blend ratio | Ultraviolet prevention effect | External appearance |
|---|---|---|---|
| Bis-N,N'-[2-(2-hydroxyethoxy)ethyl]-4-methoxybenzilidene malonamide | 10 | ⊚ | Clear and colorless |
|  | 5 | ⊚ | Clear and colorless |
|  | 1 | ⊚ | Clear and colorless |
| Sodium 2-hydroxy-4-methoxy-5-sulfoxonium benzophenone | 10 | —* | Did not dissolve |
|  | 5 | Δ | Yellow and clear** |
|  | 1 | Δ | Yellow and clear |
| Not added | — | X | Clear and colorless |

*Measurement was not conducted because the ultraviolet absorbent did not dissolve.
**Crystals precipitated during low temperature storage.

TABLE 4

(b) Cream

| Ultraviolet absorbent | Blend ratio | Ultraviolet prevention effect | External appearance |
|---|---|---|---|
| Bis-N,N'-[2-(2-hydroxyethoxy)ethyl]-4-methoxybenzilidene malonamide | 10 | ⊚ | White |
|  | 5 | ⊚ | White |
|  | 1 | ⊚ | White |
| Sodium 2-hydroxy-4-methoxy-5-sulfoxonium benzophenone | 10 | —* | Did not dissolve |
|  | 5 | Δ | Yellow** |
|  | 1 | Δ | Yellow |
| Not added | — | X | White |

*Measurement was not conducted because the ultraviolet absorbent did not dissolve.
**Crystals precipitated during low temperature storage.

As clearly shown in Tables 3 and 4, the external preparations containing the ultraviolet absorbent of the present invention had a superior ultraviolet prevention effect compared with those containing a conventional water soluble ultraviolet absorbent. Also, no precipitation of the ultraviolet absorbent was observed at all during low temperature storage.

As described thus far, the ultraviolet absorbent of the present invention (bis-N,N'-[2-(2-hydroxyethoxy)ethyl]-4-methoxybenzilidene malonamide) is highly soluble in water and has superior absorption capacity over a wide ultraviolet wavelength range.

Also, it is white because it does not absorb the visible light of 400 nm or more and its aqueous solution is clear and colorless; therefore there is no problem in terms or coloring of the product.

Furthermore, since it is highly soluble in water, it can be blended into a product at a high blend ratio and even then there is no problem in terms of precipitation over time.

It does not affect the pH of the blend system.

Thus, it is an excellent water soluble ultraviolet absorbent.

Therefore, in order to investigate whether or not the ultraviolet absorbent of the present invention is suitable for blending into external preparations, more investigations were conducted on skin irritability, photostability, and the influence of inorganic powders.

Test Example 5

Skin Irritability Test

This test was conducted by using the same sample as in Test example 4 (blend ratio of the ultraviolet absorbent was 10 wt %).
<Patch Test>
A Finn chamber was used to conduct the 24-hour closed patch test on the flexor forearm of healthy male and female volunteers; a group of 20 volunteers were used and the following evaluation criteria were used.
(Evaluation Criteria)

| Degree of skin reaction | Score |
| --- | --- |
| No reaction (negative) | 0 |
| Mild erythema (suspected positive) | 1 |
| Erythema (mildly positive) | 2 |
| Erythema + edema (medium positive) | 3 |
| Erythema + edema + papule (strongly positive) | 4 |
| Large bubbles (strongest positive) | 5 |

(Assessment)
The average score was calculated and the evaluation was done based on the following criteria.
⊚: The average score is 0.
○: The average score is more than 0 and less than 1.
Δ: The average score is 1 or more and less than 2.
X: The average score is 2 or more.
<Results>
The results are shown in Table 5.

TABLE 5

| Ultraviolet absorbent | Formulation | Evaluation |
| --- | --- | --- |
| Bis-N,N'-[2-(2-hydroxyethoxy) ethyl]-4-methoxybenzilidene malonamide | Lotion | ⊚ |
| | Cream | ⊚ |
| Not added | Lotion | ⊚ |
| | Cream | ⊚ |

As clearly shown in Table 5, the external preparation containing the ultraviolet absorbent of the present invention did not exhibit any skin irritability at all in the patch test, confirming its excellent safety.

Test Example 6

Photostability Test

A solution of the ultraviolet absorbent of the present invention was exposed to sunlight for two weeks (sunlight exposure level 80 MJ/m$^2$) and then the residual ratio and changes in the appearance were investigated and the ultraviolet absorption spectrum was measured (solvent: water, concentration 10 ppm, optical path length 1 cm) by using a spectrophotometer; the ultraviolet absorption spectrum was integrated over a range of 290-400 nm to obtain the area value, which was compared with the value before the sunlight exposure.
(Evaluation)
Changes in the residual ratio and the area value of the ultraviolet absorption spectrum were evaluated based on the following criteria.
⊚: 95% or more of the value before the sunlight exposure.
○: 90% or more and less than 95% of the value before the sunlight exposure.
Δ: 70% or more and less than 90% of the value before the sunlight exposure.
X: Less than 70% of the value before the sunlight exposure.
<Results>
The results are shown in Table 6.

TABLE 6

| Ultraviolet absorbent | Residual ratio | External appearance | Changes in the area value of the ultraviolet absorption spectrum |
| --- | --- | --- | --- |
| Bis-N,N'-[2-(2-hydroxyethoxy)ethyl]-4-methoxybenzilidene malonamide | ⊚ | Clear and colorless | ⊚ |
| Sodium 2-hydroxy-4-methoxy-5-sulfoxonium benzophenone | ○ | Yellow and clear | ○ |

As clearly shown in Table 6, the ultraviolet absorbent of the present invention, compared with the conventional water soluble ultraviolet absorbent, was not decomposed even by long time exposure to direct sunlight and exhibited a very high residual ratio.

Also, there was no change in the shape and area value of the ultraviolet spectrum and, in terms of external appearance, no coloring or precipitation was observed.

Test Example 7

Stability Test for use in Combination with an Inorganic Powder Ultraviolet Shielding Agent Sunscreen cream was prepared according to the following recipe; it was stored at 50° C. for two months and visually observed for discoloration to investigate the stability when used in combination with an inorganic powder ultraviolet shielding agent.

"Sunscreen Cream"

| | | |
|---|---|---|
| (1) Ethyl cellulose | 1.0 wt % |
| (2) Ethanol | 5.0 |
| (3) 2-ethylhexyl succinate | 24.0 |
| (4) Titanium dioxide | 1.0 |
| (5) Porous silicic acid anhydride | 1.0 |
| (6) Spherical nylon powder | 1.0 |
| (7) Talc | 1.0 |
| (8) Sericite | 1.0 |
| (9) Boron nitride | 1.0 |
| (10) Silicone-treated mica | 1.0 |
| (11) Ultraviolet absorbent | 10.0 |
| (12) Carboxymethyl cellulose | 1.0 |
| (13) Ion-exchanged water | Balance |
| (14) Preservative | Appropriate amount |
| (15) Perfume | Appropriate amount |

<Preparation Method>

After adding (2) to (1) and letting full swelling occur, (3)-(10) were added, followed by heating and mixing for thorough dispersion and dissolution. This dispersion liquid was maintained at 70° C. and a mixed solution of (11)-(15) was gradually added as homogeneous emulsification was carried out by using a homomixer, followed by thorough stirring and cooling down to 30° C. to obtain sunscreen cream.

The results are shown in Table 7.

TABLE 7

| Ultraviolet absorbent | Discoloration |
|---|---|
| Bis-N,N'-[2-(2-hydroxyethoxy) ethyl]-4-methoxybenzilidene malonamide | None |
| Sodium 2-hydroxy-4-methoxy-5-sulfoxonium benzophenone | Discolored to dark yellow |

As clearly shown in Table 7, the conventional water soluble ultraviolet absorbent discolored to dark yellow when used in combination with an inorganic powder but the ultraviolet absorbent of the present invention did not exhibit discoloration even when it was used in combination with an inorganic powder.

As described thus far, the ultraviolet absorbent of the present invention (bis-N,N'-[2-(2-hydroxyethoxy)ethyl]-4-methoxybenzilidene malonamide) does not exhibit skin irritability, has superior photostability, and does not discolor even when used in combination with an inorganic powder.

Therefore, the ultraviolet absorbent of the present invention is very useful as an ultraviolet absorbent that can be added to an external preparation.

Examples of the external preparation of the present invention are listed below, but the present invention is not limited to these. The blend ratios are expressed as a wt %.

Example 2

Lotion

| (Alcohol phase) | |
|---|---|
| Ethanol | 10.0 |
| Oleyl alcohol | 0.1 |
| POE (20) sorbitan monolaurate | 0.5 |
| POE(15) lauryl ether | 0.5 |
| Preservative | Appropriate amount |
| Perfume | Appropriate amount |
| (Water phase) | |
| Bis-N,N'-[2-(2-hydroxyethoxy) ethyl]-4-methoxybenzilidene malonamide | 10.0 |
| 2-phenylbenzimidazole-5-sulfonic acid | 3.0 |
| Sodium hydroxide | 0.4 |
| 1,3-butylene glycol | 6.0 |
| Glycerin | 4.0 |
| 4,5-dimorpholino-3-hydroxypyridazine | 0.3 |
| Ion-exchanged water | Balance |

(Preparation Method)

The water phase and the alcohol phase were separately prepared and then mixed together.

Example 3

Lotion

| (Alcohol phase) | |
|---|---|
| Ethanol | 10.0 |
| Oleyl alcohol | 0.1 |
| POE (20) sorbitan monolaurate | 0.5 |
| POE(15) lauryl ether | 0.5 |
| Preservative | Appropriate amount |
| Perfume | Appropriate amount |
| (Water phase) | |
| Bis-N,N'-[2-(2-hydroxyethoxy) ethyl]-4-methoxybenzilidene malonamide | 5.0 |
| 2-phenylbenzimidazole-5-sulfonic acid | 3.0 |
| Sodium hydroxide | 0.4 |
| 1,3-butylene glycol | 6.0 |
| Glycerin | 4.0 |
| Terephthalylidene dicamphor sulfonic acid | 1.0 |
| 4,5-dimorpholino-3-hydroxypyridazine | 0.3 |
| Ion-exchanged water | Balance |

(Preparation Method)

The water phase and the alcohol phase were separately prepared and then mixed together.

Example 4

Lotion

| (Alcohol phase) | |
|---|---|
| Ethanol | 10.0 |
| 2-ethylhexyl-p-methoxycinnamate | 0.5 |
| 2-hydroxy-4-methoxybenzophenone | 0.5 |
| 4-tert-butyl-4'-methoxybenzoylmethane | 0.5 |
| 2-Ethylhexyl 2-cyano-3,3-diphenylacrylate | 0.5 |
| POE(20) oleyl ether | 0.5 |
| Preservative | Appropriate amount |
| Perfume | Appropriate amount |
| (Water phase) | |
| Dipropylene glycol | 6.0 |
| Sorbit | 4.0 |
| PEG 1500 | 5.0 |
| Bis-N,N'-[2-(2-hydroxyethoxy) ethyl]-4-methoxybenzilidene malonamide | 20.0 |
| Terephthalylidene dicamphor sulfonic acid | 1.0 |
| 2-phenylbenzimidazole-5-sulfonic acid | 3.0 |
| Triethanolamine | 1.8 |
| Methylcellulose | 0.2 |
| Quince seed | 0.1 |
| Ion-exchanged water | Balance |

(Preparation Method)

Methyl cellulose and quince seed were mixed with a part of the ion-exchanged water and stirred to prepare a viscous liquid. The rest of the ion-exchanged water and the other water phase ingredients were mixed and dissolved, to which the aforementioned viscous liquid was added to obtain the homogeneous water phase. The alcohol phase was prepared and added to the water phase, followed by mixing.

Example 5

Lotion

| (Alcohol phase) | |
| --- | --- |
| Ethanol | 10.0 |
| 2-ethylhexyl-p-methoxycinnamate | 0.5 |
| 2-hydroxy-4-methoxybenzophenone | 0.5 |
| 4-tert-butyl-4'-methoxybenzoylmethane | 0.5 |
| 2-Ethylhexyl 2-cyano-3,3-diphenylacrylate | 0.5 |
| POE(20) oleyl ether | 0.5 |
| Preservative | Appropriate amount |
| Perfume | Appropriate amount |
| (Water phase) | |
| Dipropylene glycol | 6.0 |
| Sorbit | 4.0 |
| PEG 1500 | 5.0 |
| Bis-N,N'-[2-(2-hydroxyethoxy) ethyl]-4-methoxybenzilidene malonamide | 7.0 |
| 2-phenylbenzimidazole-5-sulfonic acid | 3.0 |
| Triethanolamine | 1.8 |
| Methylcellulose | 0.2 |
| Quince seed | 0.1 |
| Ion-exchanged water | Balance |

(Preparation Method)

Methylcellulose and quince seed were mixed with a part of the ion-exchanged water and stirred to prepare a viscous liquid. The rest of the ion-exchanged water and the other water phase ingredients were mixed and dissolved, to which the aforementioned viscous liquid was added to obtain the homogeneous water phase. The alcohol phase was prepared and added to the water phase, followed by mixing.

Example 6

Cream

| Stearic acid | 5.0 |
| --- | --- |
| Stearyl alcohol | 4.0 |
| Isopropyl myristate | 18.0 |
| Glyceryl monostearate | 3.0 |
| 2-ethylhexyl-p-methoxycinnamate | 10.0 |
| 2-hydroxy-4-methoxybenzophenone | 5.0 |
| 4-tert-butyl-4'-methoxybenzoylmethane | 3.0 |
| 2-ehylhexyl 2-cyano-3,3-diphenylacrylate | 5.0 |
| Propylene glycol | 10.0 |
| Bis-N,N'-[2-(2-hydroxyethoxy) ethyl]-4-methoxybenzilidene malonamide | 5.0 |
| Terephthalylidene dicamphor sulfonic acid | 0.5 |
| 2-phenylbenzimidazole-5-sulfonic acid | 3.0 |
| Triethanolamine | 1.8 |
| 4,5-dimorpholino-3-hydroxypyridazine | 0.2 |
| Potassium hydroxide | 0.2 |
| Sodium hydrogen sulfite | 0.01 |
| Preservative | Appropriate amount |
| Perfume | Appropriate amount |
| Ion-exchanged water | Balance |

(Preparation Method)

The water phase ingredients were added and dissolved in ion-exchanged water and the temperature was raised to 70° C. and maintained (water phase). Other ingredients were mixed, heated and melted, and the temperature was maintained at 70° C. (oil phase). The oil phase was gradually added to the water phase and pre-emulsification was carried out; the mixture was homogeneously emulsified by using a homomixer, followed by thorough stirring and cooling down to 30° C.

Example 7

Cream

| Stearic acid | 5.0 |
| --- | --- |
| Stearyl alcohol | 4.0 |
| Isopropyl myristate | 18.0 |
| Glyceryl monostearate | 3.0 |
| 2-ethylhexyl-p-methoxycinnamate | 10.0 |
| 2-hydroxy-4-methoxybenzophenone | 5.0 |
| 4-tert-butyl-4'-methoxybenzoylmethane | 3.0 |
| 2-ethylhexyl 2-cyano-3,3-diphenylacrylate | 10.0 |
| Propylene glycol | 10.0 |
| Bis-N,N'-[2-(2-hydroxyethoxy) ethyl]-4-methoxybenzilidene malonamide | 3.0 |
| 2-phenylbenzimidazole-5-sulfonic acid | 3.0 |
| Sodium hydroxide | 0.4 |
| Terephthalylidene dicamphor sulfonic acid | 0.5 |
| 4,5-dimorpholino-3-hydroxypyridazine | 0.2 |
| Potassium hydroxide | 0.2 |
| Sodium hydrogen sulfite | 0.01 |
| Preservative | Appropriate amount |
| Perfume | Appropriate amount |
| Ion-exchanged water | Balance |

(Preparation Method)

The water phase ingredients were added and dissolved in ion-exchanged water and the temperature was raised to 70° C. and maintained (water phase). The other ingredients were mixed, heated and melted, and the temperature was maintained at 70° C. (oil phase). The oil phase was gradually added to the water phase and pre-emulsification was carried out; the mixture was homogeneously emulsified by using a homo-mixer, followed by thorough stirring and cooling down to 30° C.

Example 8

Cream

| Stearic acid | 6.0 |
| --- | --- |
| Sorbitan monostearate | 2.0 |
| POE (20) sorbitan monolaurate | 1.5 |
| Propylene glycol | 10.0 |
| Bis-N,N'-[2-(2-hydroxyethoxy) ethyl]-4-methoxybenzilidene malonamide | 10.0 |
| 2-phenylbenzimidazole-5-sulfonic acid | 3.0 |
| Sodium hydroxide | 0.4 |
| Glyceryl trioctanoate | 10.0 |
| Squalane | 5.0 |
| Sodium hydrogen sulfite | 0.01 |
| Ethylparaben | 0.3 |
| Perfume | Appropriate amount |
| Ion-exchanged water | Balance |

(Preparation Method)

Propylene glycol, bis-N,N'-[2-(2-hydroxyethoxy)ethyl]-4-methoxybenzilidene malonamide, 2-phenylbenzimidazole-5-sulfonic acid, and sodium hydroxide were added and dissolved in ion-exchanged water and the temperature was raised to 70° C. and maintained (water phase). The other ingredients were mixed, heated and melted, and the temperature was maintained at 70° C. (oil phase). The oil phase was gradually added to the water phase and pre-emulsification was conducted; after a homomixer was used to emulsify the mixture homogeneously, the temperature was cooled down to 30° C. while thorough stirring was maintained.

Example 9

Cream

| | |
|---|---|
| Stearic acid | 6.0 |
| Sorbitan monostearate | 2.0 |
| POE (20) sorbitan monolaurate | 1.5 |
| Propylene glycol | 10.0 |
| Bis-N,N'-[2-(2-hydroxyethoxy) ethyl]-4-methoxybenzilidene malonamide | 5.0 |
| Glyceryl trioctanoate | 10.0 |
| Squalane | 5.0 |
| Sodium hydrogen sulfite | 0.01 |
| Ethylparaben | 0.3 |
| Perfume | Appropriate amount |
| Ion-exchanged water | Balance |

(Preparation Method)

Propylene glycol, bis-N,N'-[2-(2-hydroxyethoxy)ethyl]-4-methoxybenzilidene malonamide were added and dissolved in ion-exchanged water and the temperature was raised to 70° C. and maintained (water phase). Other ingredients were mixed, heated and melted, and the temperature was maintained at 70° C. (oil phase). The oil phase was gradually added to the water phase and pre-emulsification was conducted; after a homomixer was used to emulsify the mixture homogeneously, the temperature was cooled down to 30° C. while thorough stirring was maintained.

Example 10

Emulsion

| | |
|---|---|
| Stearic acid | 2.5 |
| Cetyl alcohol | 1.5 |
| Petrolatum | 5.0 |
| Liquid petrolatum | 10.0 |
| POE (10) monooleic ester | 2.0 |
| 2-ethylhexyl-p-methoxycinnamate | 3.0 |
| 2-hydroxy-4-methoxybenzophenone | 2.0 |
| 4-tert-butyl-4'-methoxybenzoylmethane | 2.0 |
| 2-ethylhexyl 2-cyano-3,3-diphenylacrylate | 5.0 |
| PEG 1500 | 3.0 |
| Triethanolamine | 1.0 |
| Bis-N,N'-[2-(2-hydroxyethoxy) ethyl]-4-methoxybenzilidene malonamide | 5.0 |
| 2-phenylbenzimidazole-5-sulfonic acid | 3.0 |
| Sodium hydroxide | 0.4 |
| Terephthalylidene dicamphor sulfonic acid | 0.5 |
| 4,5-dimorpholino-3-hydroxypyridazine | 0.1 |
| Sodium hydrogen sulfite | 0.01 |
| Ethylparaben | 0.3 |
| Carboxyvinyl polymer | 0.05 |
| Perfume | Appropriate amount |
| Ion-exchanged water | Balance |

(Preparation Method)

The carboxyvinyl polymer was dissolved in a small amount of ion-exchanged water (phase A). The water phase ingredients were added, heated and dissolved in the rest of the ion-exchanged water and the temperature was raised to 70° C. and maintained (water phase). The other ingredients were mixed, heated and melted, and the temperature was maintained at 70° C. (oil phase). The oil phase was added to the water phase and pre-emulsification was conducted; after phase A was added and a homomixer was used to emulsify the mixture homogeneously, the temperature was cooled down to 30° C. while thorough stirring was maintained.

Example 11

Emulsion

| | |
|---|---|
| Stearic acid | 2.5 |
| Cetyl alcohol | 1.5 |
| Petrolatum | 5.0 |
| Liquid paraffin | 10.0 |
| POE (10) monooleic ester | 2.0 |
| 2-ethylhexyl-p-methoxycinnamate | 3.0 |
| 2-hydroxy-4-methoxybenzophenone | 2.0 |
| 4-tert-butyl-4'-methoxybenzoylmethane | 2.0 |
| 2-ethylhexyl 2-cyano-3,3-diphenylacrylate | 5.0 |
| PEG 1500 | 3.0 |
| Triethanolamine | 1.0 |
| Bis-N,N'-[2-(2-hydroxyethoxy) ethyl]-4-methoxybenzilidene malonamide | 3.0 |
| 2-phenylbenzimidazole-5-sulfonic acid | 3.0 |
| Triethanolamine | 1.8 |
| Terephthalylidene dicamphor sulfonic acid | 0.5 |
| 4,5-dimorpholino-3-hydroxypyridazine | 0.1 |
| Sodium hydrogen sulfite | 0.01 |
| Ethylparaben | 0.3 |
| Carboxyvinyl polymer | 0.05 |
| Perfume | Appropriate amount |
| Ion-exchanged water | Balance |

(Preparation Method)

The carboxyvinyl polymer was dissolved in a small amount of ion-exchanged water (phase A). The water phase ingredients were added, heated and dissolved and the temperature was raised to 70° C. and maintained (water phase). The other ingredients were mixed, heated and melted, and the temperature was maintained at 70° C. (oil phase). The oil phase was added to the water phase and pre-emulsification was conducted; after phase A was added and a homomixer was used to emulsify the mixture homogeneously, the temperature was cooled down to 30° C. while thorough stirring was maintained.

Example 12

Gel

| | |
|---|---|
| 95% Ethanol | 10.0 |
| Dipropylene glycol | 15.0 |
| POE(50) oleyl ether | 2.0 |
| Carboxyvinyl polymer | 1.0 |
| Sodium hydroxide | 0.55 |
| Bis-N,N'-[2-(2-hydroxyethoxy) ethyl]-4-methoxybenzilidene malonamide | 1.0 |
| 2-phenylbenzimidazole-5-sulfonic acid | 1.0 |
| Methylparaben | 0.1 |
| Perfume | Appropriate amount |
| Ion-exchanged water | Balance |

(Preparation Method)

The carboxyvinyl polymer was dissolved homogeneously in a small amount of ion-exchanged water (phase A). POE (50) oleyl ether was dissolved in 95% ethanol, which was then added to phase A. The ingredients other than sodium hydroxide were added and then sodium hydroxide was added to neutralize and thicken the mixture.

Example 13

Gel

| | |
|---|---|
| 95% Ethanol | 10.0 |
| Dipropylene glycol | 15.0 |
| POE(50) oleyl ether | 2.0 |
| Carboxyvinyl polymer | 1.0 |
| Sodium hydroxide | 0.55 |
| Bis-N,N'-[2-(2-hydroxyethoxy) ethyl]-4-methoxybenzilidene malonamide | 5.0 |
| 2-phenylbenzimidazole-5-sulfonic acid | 1.0 |
| Methylparaben | 0.2 |
| Perfume | Appropriate amount |
| Ion-exchanged water | Balance |

(Preparation Method)

The carboxyvinyl polymer was dissolved homogeneously in ion-exchanged water (phase A). POE (50) oleyl ether was dissolved in 95% ethanol, which was then added to phase A. The ingredients other than sodium hydroxide were added and then sodium hydroxide was added to neutralize and thicken the mixture.

Example 14

Essence

| (Phase A) | |
|---|---|
| 95% Ethanol | 10.0 |
| 2-ethylhexyl-p-methoxycinnamate | 1.0 |
| 2-hydroxy-4-methoxybenzophenone | 0.5 |
| 4-tert-butyl-4'-methoxybenzoylmethane | 0.5 |
| 2-ethylhexyl 2-cyano-3,3-diphenylacrylate | 0.5 |
| POE (20) octyldodecanol | 1.0 |
| Methylparaben | 0.15 |
| Pantothenylethyl ether | 0.1 |
| (Phase B) | |
| Potassium hydroxide | 0.1 |
| (Phase C) | |
| Bis-N,N'-[2-(2-hydroxyethoxy) ethyl]-4-methoxybenzilidene malonamide | 10.0 |
| 2-phenylbenzimidazole-5-sulfonic acid | 3.0 |
| Sodium hydroxide | 0.4 |
| Glycerin | 5.0 |
| Dipropylene glycol | 10.0 |
| Terephthalylidene dicamphor sulfonic acid | 2.0 |
| Sodium hydrogen sulfite | 0.03 |
| Carboxyvinyl polymer | 0.2 |
| Ion-exchanged water | Balance |

(Preparation Method)

Phase A and phase C were separately dissolved homogeneously and phase A was added to phase C and then solubilized. Phase B was then added and mixed.

Example 15

Essence

| (Phase A) | |
|---|---|
| 95% Ethanol | 10.0 |
| 2-ethylhexyl-p-methoxycinnamate | 1.0 |
| 2-hydroxy-4-methoxybenzophenone | 0.5 |
| 4-tert-butyl-4'-methoxybenzoylmethane | 0.5 |
| 2-ethylhexyl 2-cyano-3,3-diphenylacrylate | 0.5 |
| POE (20) octyldodecanol | 1.0 |
| Methylparaben | 0.15 |
| Pantothenylethyl ether | 0.1 |
| (Phase B) | |
| Potassium hydroxide | 0.1 |
| (Phase C) | |
| Bis-N,N'-[2-(2-hydroxyethoxy) ethyl]-4-methoxybenzilidene malonamide | 5.0 |
| 2-phenylbenzimidazole-5-sulfonic acid | 3.0 |
| Triethanolamine | 1.8 |
| Glycerin | 5.0 |
| Dipropylene glycol | 10.0 |
| Terephthalylidene dicamphor sulfonic acid | 3.0 |
| Sodium hydrogen sulfite | 0.03 |
| Carboxyvinyl polymer | 0.2 |
| Ion-exchanged water | Balance |

(Preparation Method)

Phase A and phase C were separately dissolved homogeneously and phase A was added to phase C and then solubilized. Phase B was then added and mixed.

Example 16

Self Tanning Emulsion

| (Part 1) | |
|---|---|
| 2-ethylhexyl 2-cyano-3,3-diphenylacrylate | 5.0 |
| PEG-5 glyceryl stearate | 1.0 |
| PEG-60 glyceryl stearate | 2.0 |
| Cyclomethicone | 5.0 |
| Diisopropyl sebacate | 5.0 |
| Behenyl alcohol | 2.0 |
| Stearyl alcohol | 1.0 |
| Hydrogenated palm oil | 2.0 |
| Perfume | Appropriate amount |
| (Part 2) | |
| Bis-N,N'-[2-(2-hydroxyethoxy) ethyl]-4-methoxybenzilidene malonamide | 5.0 |
| Dihydroxyacetone | 5.0 |
| Dipotassium glycyrrhizinate | 0.01 |
| Ethanol | 5.0 |
| 1,3-butylene glycol | 5.0 |
| EDTA-3Na | 0.1 |
| Sodium pyrosulfite | 0.1 |
| Paraben | Appropriate amount |
| Ion-exchanged water | Balance |

(Preparation Method)

Part 2 was homogeneously dissolved at 60° C., into which Part 1, homogeneously dissolved at 70° C., was added, followed by the emulsification treatment. The mixture was then cooled down to obtain a self tanning emulsion.

Example 17

Pack

| (Phase A) | |
|---|---|
| Dipropylene glycol | 5.0 |
| POE(60) hydrogenated castor oil | 5.0 |
| (Phase B) | |
| Olive oil | 5.0 |
| Tocopherol acetate | 0.2 |
| Ethylparaben | 0.2 |
| Perfume | 0.2 |
| (Phase C) | |
| Bis-N,N'-[2-(2-hydroxyethoxy) ethyl]-4-methoxybenzilidene malonamide | 0.1 |
| Sodium hydrogen sulfite | 0.03 |
| Polyvinyl alcohol (degree of saponification 90, degree of polymerization 2,000) | 13.0 |
| Ethanol | 7.0 |
| Ion-exchanged water | Balance |

(Preparation Method)

Phase A, phase B, and phase C were separately dissolved homogeneously and phase B was added to phase A and then solubilized. This was then added to phase C, followed by mixing.

Example 18

Pack

| (Phase A) | |
|---|---|
| Dipropylene glycol | 5.0 |
| POE(60) hydrogenated castor oil | 5.0 |
| (Phase B) | |
| Olive oil | 5.0 |
| Tocopherol acetate | 0.2 |
| Ethylparaben | 0.2 |
| Perfume | 0.2 |
| (Phase C) | |
| Bis-N,N'-[2-(2-hydroxyethoxy) ethyl]-4-methoxybenzilidene malonamide | 0.1 |
| 2-phenylbenzimidazole-5-sulfonic acid | 0.3 |
| Triethanolamine | 0.18 |
| Sodium hydrogen sulfite | 0.03 |
| Polyvinyl alcohol (degree of saponification 90, degree of polymerization 2,000) | 13.0 |
| Ethanol | 7.0 |
| Ion-exchanged water | Balance |

(Preparation Method)

Phase A, phase B, and phase C were separately dissolved homogeneously and phase B was added to phase A and then solubilized. This was then added to phase C, followed by mixing.

Example 19

Emulsion

| (Oil phase) | |
|---|---|
| Stearyl alcohol | 1.5 |
| Squalane | 2.0 |
| Petrolatum | 2.5 |
| Deodorizing liquid lanolin | 1.5 |
| Evening primrose oil | 2.0 |
| Isopropyl myristate | 5.0 |
| Glyceryl monooleate | 2.0 |
| 2-ethylhexyl 2-cyano-3, 3-diphenylacrylate | 5.0 |
| POE (60) hydrogenated castor oil | 2.0 |
| Tocopherol acetate | 0.05 |
| Ethylparaben | 0.2 |
| Methylparaben | 0.1 |
| Perfume | Appropriate amount |
| (Water phase) | |
| Bis-N,N'-[2-(2-hydroxyethoxy) ethyl]-4-methoxybenzilidene malonamide | 5.0 |
| 4,5-dimorpholino-3-hydroxypyridazine | 0.05 |
| Sodium hydrogen sulfite | 0.01 |
| Glycerin | 5.0 |
| Sodium hyaluronate | 0.01 |
| Carboxyvinyl polymer | 0.2 |
| Potassium hydroxide | 0.2 |
| Ion-exchanged water | Balance |

(Preparation Method)

The oil phase and the water phase were separately dissolved at 70° C. and the oil phase was mixed into the water phase; the mixture was then emulsified by using an emulsifier and cooled down to 30° C. with a heat exchanger.

Example 20

Solid Powdery Foundation

| (1) Talc | 15.0 |
|---|---|
| (2) Sericite | 10.0 |
| (3) Spherical nylon powder | 10.0 |
| (4) Porous silicic acid anhydride | 15.0 |
| (5) Boron nitride | 5.0 |
| (6) Titanium dioxide | 5.0 |
| (7) Iron oxide | 3.0 |
| (8) Zinc stearate | 5.0 |
| (9) Bis-N,N'-[2-(2-hydroxyethoxy) ethyl]-4-methoxybenzilidene malonamide | 1.0 |
| (10) Liquid paraffin | Balance |
| (11) 2-ethylhexyl 2-cyano-3,3-diphenylacrylate | 1.0 |
| (12) Glyceryl triisooctanoate | 15.0 |
| (13) Sorbitan sesquioleate | 1.5 |
| (14) Preservative | Appropriate amount |
| (15) Perfume | Appropriate amount |

(Preparation Method)

Ingredients (1)-(8) were mixed and crushed. To this a mixture of (9)-(15) were added, followed by stirring and mixing. This was molded into a container to obtain a solid foundation.

Example 21

Solid Powdery Foundation

| (1) Talc | 15.0 |
|---|---|
| (2) Sericite | 10.0 |
| (3) Spherical nylon powder | 10.0 |

|     |     |     |
| --- | --- | --- |
| (4) | Porous silicic acid anhydride | 15.0 |
| (5) | Boron nitride | 5.0 |
| (6) | Titanium dioxide | 5.0 |
| (7) | Iron oxide | 3.0 |
| (8) | Zinc stearate | 5.0 |
| (9) | Bis-N,N'-[2-(2-hydroxyethoxy) ethyl]-4-methoxybenzilidene malonamide | 1.0 |
| (10) | Liquid paraffin | Balance |
| (11) | Glyceryl triisooctanoale | 15.0 |
| (12) | Sorbitan sesquioleate | 1.5 |
| (13) | Preservative | Appropriate amount |
| (14) | Perfume | Appropriate amount |

(Preparation Method)

Ingredients (1)-(8) were mixed and crushed. To this a mixture of (9)-(15) were added, followed by stirring and mixing. This was molded into a container to obtain a solid foundation.

Example 22

Water-in-Oil Emulsified Foundation

|     |     |     |
| --- | --- | --- |
| (1) | Spherical nylon | 10.0 |
| (2) | Porous silicic acid anhydride | 8.0 |
| (3) | Titanated mica | 2.0 |
| (4) | Silicone-treated sericite | 2.0 |
| (5) | Silicone-treated mica | 12.0 |
| (6) | Silicone-treated titanium dioxide | 5.0 |
| (7) | Silicone-treated iron oxide | 2.0 |
| (8) | Ion-exchanged water | Balance |
| (9) | Bis-N,N'-[2-(2-hydroxyethoxy) ethyl]-4-methoxybenzilidene malonamide | 5.0 |
| (10) | Decamethylcyclopentasiloxane | 18.0 |
| (11) | Dimethylpolysiloxane | 5.0 |
| (12) | Squalane | 1.0 |
| (13) | Polyoxyethylene modified dimethylpolysiloxane | 2.0 |
| (14) | 2-ethylhexyl-p-methoxycinnamate | 3.0 |
| (15) | 2-hydroxy-4-methoxybenzophenone | 1.0 |
| (16) | 4-tert-butyl-4'-methoxybenzoylmethane | 0.5 |
| (17) | Terephthalylidene dicamphor sulfonic acid | 0.5 |
| (18) | 2-ethylhexyl 2-cyano-3,3-diphenylacrylate | 0.5 |
| (19) | Preservative | Appropriate amount |
| (20) | Perfume | Appropriate amount |

(Preparation Method)

Ingredients (10)-(20) were homogeneously mixed and dissolved. To this, (1)-(7), mixed and crushed, were added and dispersed. (9) was dissolved into (8), which was then added to this dispersion liquid, followed by emulsification. This was put into a container to obtain a water-in-oil emulsified foundation.

Example 23

Water-in-Oil Emulsified Foundation

|     |     |     |
| --- | --- | --- |
| (1) | Spherical nylon | 10.0 |
| (2) | Porous silicic acid anhydride | 8.0 |
| (3) | Titanated mica | 2.0 |
| (4) | Silicone-treated sericite | 2.0 |
| (5) | Silicone-treated mica | 12.0 |
| (6) | Silicone-treated titanium dioxide | 5.0 |
| (7) | Silicone-treated iron oxide | 2.0 |
| (8) | Ion-exchanged water | Balance |
| (9) | Bis-N,N'-[2-(2-hydroxyethoxy) ethyl]-4-methoxybenzilidene malonamide | 3.0 |
| (10) | Decamethylcyclopentasiloxane | 18.0 |
| (11) | Dimethylpolysiloxane | 5.0 |
| (12) | Squalane | 1.0 |
| (13) | Polyoxyethylene modified dimethylpolysiloxane | 2.0 |
| (14) | 2-ethylhexyl-p-methoxycinnamate | 3.0 |
| (15) | 2-hydroxy-4-methoxybenzophenone | 1.0 |
| (16) | 4-tert-butyl-4'-methoxybenzoylmethane | 0.5 |
| (17) | Terephthalylidene dicamphor sulfonic acid | 0.5 |
| (18) | 2-ethylhexyl 2-cyano-3,3-diphenylacrylate | 0.5 |
| (19) | Preservative | Appropriate amount |
| (20) | Perfume | Appropriate amount |

(Preparation Method)

Ingredients (10)-(20) were homogeneously mixed and dissolved. To this, (1)-(7), mixed and crushed, were added and dispersed. (9) was dissolved into (8), which was then added to this dispersion liquid, followed by emulsification. This was put into a container to obtain a water-in-oil emulsified foundation.

Example 24

Face Powder

|     |     |     |
| --- | --- | --- |
| (1) | Talc | Balance |
| (2) | Sericite | 10.0 |
| (3) | Spherical nylon powder | 10.0 |
| (4) | Boron nitride | 5.0 |
| (5) | Iron oxide | 3.0 |
| (6) | Magnesium carbonate | 5.0 |
| (7) | Squalane | 3.0 |
| (8) | Glyceryl triisooctanoate | 2.0 |
| (9) | Sorbitan sesquioleate | 2.0 |
| (10) | 2-ethylhexyl 2-cyano-3,3-diphenylacrylate | 0.5 |
| (11) | Bis-N,N'-[2-(2-hydroxyethoxy) ethyl]-4-methoxybenzilidene malonamide | 0.5 |
| (12) | Preservative | Appropriate amount |
| (13) | Perfume | Appropriate amount |

(Preparation Method)

Ingredients (1)-(6) were mixed and crushed. To this a mixture of (7)-(13) were added, followed by stirring and mixing to obtain face powder.

Example 25

Eye Shadow

|     |     |     |
| --- | --- | --- |
| (1) | Talc | Balance |
| (2) | Mica | 15.0 |
| (3) | Spherical nylon powder | 10.0 |
| (4) | Boron nitride | 5.0 |
| (5) | Iron oxide | 3.0 |
| (6) | Titanium oxide-coated mica | 5.0 |
| (7) | Squalane | 3.0 |
| (8) | Glyceryl triisooctanoate | 2.0 |
| (9) | Sorbitan sesquioleate | 2.0 |
| (10) | 2-ethylhexyl 2-cyano-3,3-diphenylacrylate | 1.0 |
| (11) | Bis-N,N'-[2-(2-hydroxyethoxy) ethyl]-4-methoxybenzilidene malonamide | 0.3 |
| (12) | Preservative | Appropriate amount |
| (13) | Perfume | Appropriate amount |

(Preparation Method)

Ingredients (1)-(6) were mixed and crushed. To this a mixture of (7)-(13) were added, followed by stirring and mixing to obtain eye shadow.

Example 26

Lipstick

| | | |
|---|---|---|
| (1) Carnauba wax | 0.5 | |
| (2) Candelilla wax | 5.0 | |
| (3) Ceresin | 10.0 | |
| (4) Squalane | Balance | |
| (5) Glyceryl triisooctanoate | 10.0 | |
| (6) Glyceryl diisooctanoate | 20.0 | |
| (7) Terephthalylidene dicamphor sulfonic acid | 0.5 | |
| (8) 2-ethylhexyl-p-methoxycinnamate | 3.0 | |
| (9) 2-ethylhexyl 2-cyano-3,3-diphenylacrylate | 5.0 | |
| (10) Bis-N,N'-[2-(2-hydroxyethoxy) ethyl]-4-methoxybenzilidene malonamide | 3.0 | |
| (11) Cholesteryl macadamiate | 4.0 | |
| (12) Synthetic sodium magnesium silicate | 0.5 | |
| (13) Hydrophobic silica | 0.5 | |
| (14) Ion-exchanged water | 2.0 | |
| (15) Coloring agent | Appropriate amount | |
| (16) Preservative | Appropriate amount | |
| (17) Perfume | Appropriate amount | |

(Preparation Method)

(11) was heated up to 60° C., into which (12) and (13) were dispersed; to this (10) and (14) were added, followed by thorough stirring. This was added to separately heated and dissolved (1)-(9), followed by thorough stirring. To this (15)-(17) were added, and after dispersing and stirring the mixture was molded to obtain a lipstick.

Example 27

Lipstick

| | | |
|---|---|---|
| (1) Carnauba wax | 0.5 | |
| (2) Candelilla wax | 5.0 | |
| (3) Ceresin | 10.0 | |
| (4) Squalane | Balance | |
| (5) Glyceryl diisooctanoate | 10.0 | |
| (6) Glyceryl triisooctanoate | 20.0 | |
| (7) Terephthalylidene dicamphor sulfonic acid | 0.5 | |
| (8) 2-ethylhexyl-p-methoxycinnamate | 3.0 | |
| (9) 2-ethylhexyl 2-cyano-3,3-diphenylacrylate | 5.0 | |
| (10) Bis-N,N'-[2-(2-hydroxyethoxy) ethyl]-4-methoxybenzilidene malonamide | 2.0 | |
| (11) 2-phenylbenzimidazole-5-sulfonic acid | 3.0 | |
| (12) Sodium hydroxide | 0.4 | |
| (13) Cholesteryl macadamiate | 4.0 | |
| (14) Synthetic sodium magnesium silicate | 0.5 | |
| (15) Hydrophobic silica | 0.5 | |
| (16) Ion-exchanged water | 2.0 | |
| (17) Coloring agent | Appropriate amount | |
| (18) Preservative | Appropriate amount | |
| (19) Perfume | Appropriate amount | |

(Preparation Method)

(13) was heated up to 60° C., into which (14) and (15) were dispersed; to this (10), (11), (12) and (16) were added, followed by thorough stirring. This was added to separately heated and dissolved (1)-(9), followed by thorough stirring. To this (17)-(19) were added, and after dispersing and stirring the mixture was molded to obtain a lipstick.

Example 28

Hair Foam

| (Stock solution recipe) | |
|---|---|
| (1) Acrylic resin alkanol amine solution (50%) | 8.0 |
| (2) Polyoxyethylene hydrogenated castor oil | Appropriate amount |
| (3) Liquid paraffin | 5.0 |
| (4) Glycerin | 3.0 |
| (5) Perfume | Appropriate amount |
| (6) Preservative | Appropriate amount |
| (7) Ethanol | 15.0 |
| (8) Bis-N,N'-[2-(2-hydroxyethoxy) ethyl]-4-methoxybenzilidene malonamide | 7.0 |
| (9) Ion-exchanged water | Balance |
| (Filler recipe) | |
| (1) Stock solution | 90.0 |
| (2) Liquefied petroleum gas | 10.0 |

(Preparation Method)

Liquid paraffin was added to dissolved glycerin and polyoxyethylene hydrogenated castor oil and then homogeneously emulsified with a homomixer. This was added to a solution of other ingredients. Filling was done by putting the stock solution into a can, which, after installing the valve, was filled with the gas.

Example 29

Hair Foam

| (Stock solution recipe) | |
|---|---|
| (1) Acrylic resin alkanol amine solution (50%) | 8.0 |
| (2) Polyoxyethylene hydrogenated castor oil | Appropriate amount |
| (3) Liquid paraffin | 5.0 |
| (4) Glycerin | 3.0 |
| (5) Perfume | Appropriate amount |
| (6) Preservative | Appropriate amount |
| (7) Ethanol | 15.0 |
| (8) Bis-N,N'-[2-(2-hydroxyethoxy) ethyl]-4-methoxybenzilidene malonamide | 3.0 |
| (9) Ion-exchanged water | Balance |
| (Filler recipe) | |
| (1) Stock solution | 90.0 |
| (2) Liquefied petroleum gas | 10.0 |

(Preparation Method)

Liquid paraffin was added to dissolved glycerin and polyoxyethylene hydrogenated castor oil and then homogeneously emulsified with a homomixer. This was added to a solution of the other ingredients. Filling was done by putting the stock solution into a can, which, after installing the valve, was filled with the gas.

Example 30

Hair Liquid

| | | |
|---|---|---|
| (1) | Polyoxypropylene (40) butyl ether | 20.0 |
| (2) | Polyoxyethylene hydrogenated castor | 1.0 |
| (3) | Ethanol | 50.0 |
| (4) | Perfume | Appropriate amount |
| (5) | Preservative | Appropriate amount |
| (6) | 2-ethylhexyl-p-methoxycinnamate | 2.0 |
| (7) | 2-ethylhexyl 2-cyano-3,3-diphenylacrylate | 5.0 |
| (8) | Dye | Appropriate amount |
| (9) | Bis-N,N'-[2-(2-hydroxyethoxy) ethyl]-4-methoxybenzilidene malonamide | 2.0 |
| (10) | Ion-exchanged water | Balance |

(Preparation Method)

Polyoxypropylene (40) butyl ether, polyoxyethylene hydrogenated castor oil, perfume, preservative, 2-ethylhexyl-p-methoxycinnamate, and 2-ethylhexyl 2-cyano-3,3-diphenylacrylate were dissolved in ethanol. Bis-N,N'-[2-(2-hydroxyethoxy)ethyl]-4-methoxybenzilidene malonamide and the dye were dissolved in ion-exchanged water. The water phase was added to the ethanol phase, followed by filtering using filter paper.

Example 31

Hair Spray

| (Stock solution recipe) | | |
|---|---|---|
| (1) | Acrylic resin alkanol amine solution (50%) | 7.0 |
| (2) | Cetyl alcohol | 0.1 |
| (3) | Silicone oil | 0.3 |
| (4) | Ethanol | Balance |
| (5) | Perfume | Appropriate amount |
| (6) | Bis-N,N'-[2-(2-hydroxyethoxy) ethyl]-4-methoxybenzilidene malonamide | 1.0 |
| (7) | Ion-exchanged water | 3.0 |
| (Filler recipe) | | |
| (1) | Stock solution | 50.0 |
| (2) | Liquefied petroleum gas | 50.0 |

(Preparation Method)

The other ingredients were added to the ethanol and dissolved, followed by filtering. Filling was done by putting the stock solution into a can, which, after installing the valve, was filled with the gas.

Example 32

Hair Tonic

| | | |
|---|---|---|
| (1) | Bis-N,N'-[2-(2-hydroxyethoxy) ethyl]-4-methoxybenzilidene malonamide | 3.0 |
| (2) | Hydrogenated castor oil ethylene oxide (40 mole) adduct | 2.0 |
| (3) | 2-ethylhexyl-p-methoxycinnamate | 3.0 |
| (4) | 2-hydroxy-4-methoxybenzophenone | 3.0 |
| (5) | 4-tert-butyl-4'-methoxybenzoylmethane | 3.0 |
| (6) | Terephthalylidene dicamphor sulfonic acid | 1.0 |
| (7) | 2-ethylhexyl 2-cyano-3,3-diphenylacrylate | 5.0 |
| (8) | 2-phenylbenzimidazole-5-sulfonic acid | 3.0 |
| (9) | Triethanolamine | 1.8 |
| (10) | Ethanol | 60.0 |
| (11) | Perfume | Appropriate amount |
| (12) | Ion-exchanged water | Balance |

(Preparation Method)

Hydrogenated castor oil ethylene oxide (40 mole) adduct, 2-ethylhexyl-p-methoxycinnamate, 2-hydroxy-4-methoxybenzophenone, 4-tert-butyl-4'-methoxybenzoylmethane, terephthalylidene dicamphor sulfonic acid, and 2-ethylhexyl 2-cyano-3,3-diphenylacrylate were dissolved in the ethanol. Bis-N,N'-[2-(2-hydroxyethoxy)ethyl]-4-methoxybenzilidene malonamide, 2-phenylbenzimidazole-5-sulfonic acid, and triethanolamine were dissolved in ion-exchanged water. The ethanol phase and the water phase were mixed, to which the perfume was added.

Example 33

Hair Tonic

| | | |
|---|---|---|
| (1) | Bis-N,N'-[2-(2-hydroxyethoxy) ethyl]-4-methoxybenzilidene malonamide | 2.0 |
| (2) | 2-phenylbenzimidazole-5-sulfonic acid | 3.0 |
| (3) | Sodium hydroxide | 0.4 |
| (4) | Hydrogenated castor oil ethylene oxide (40 mole) adduct | 2.0 |
| (5) | 2-ethylhexyl-p-methoxycinnamate | 3.0 |
| (6) | 2-hydroxy-4-methoxybenzophenone | 3.0 |
| (7) | 4-tert-butyl-4'-methoxybenzoylmethane | 3.0 |
| (8) | 2-ethylhexyl 2-cyano-3,3-diphenylacrylate | 5.0 |
| (9) | Ethanol | 60.0 |
| (10) | Perfume | Appropriate amount |
| (11) | Ion-exchanged water | Balance |

(Preparation Method)

Hydrogenated castor oil ethylene oxide (40 mole) adduct, 2-ethylhexyl-p-methoxycinnamate, 2-hydroxy-4-methoxybenzophenone, 4-tert-butyl-4'-methoxybenzoylmethane, and 2-ethylhexyl 2-cyano-3,3-diphenylacrylate were dissolved in the ethanol. Bis-N,N'-[2-(2-hydroxyethoxy)ethyl]-4-methoxybenzilidene malonamide, 2-phenylbenzimidazole-6-sulfonic acid, and sodium hydroxide were dissolved in ion-exchanged water. The ethanol phase and the water phase were mixed, to which the perfume was added.

INDUSTRIAL APPLICABILITY

The new benzilidene malonamide and its salt of the present invention are very useful as an ultraviolet absorbent.

The ultraviolet absorbent of the present invention is highly water soluble and can be blended in water based products. It also has exceptional ultraviolet light absorption capacity over a wide region of the ultraviolet wavelengths and is useful as a highly safe and stable ultraviolet absorbent.

Therefore, by blending it in, an ultraviolet absorbing composition and/or external preparation having a high ultraviolet prevention effect as well as superior safety and stability can be obtained.

Furthermore, it does not absorb the visible region and does not have a problem in terms of coloring, and therefore it can be blended into various products.

The invention claimed is:

1. A benzilidene malonamide compound represented by the following formula (1) and salts thereof

[Chemical formula 1]

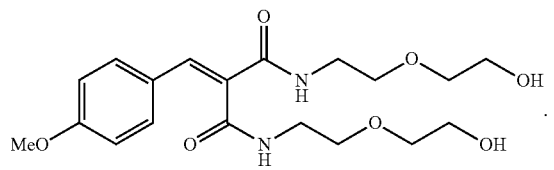

(1)

2. An ultraviolet absorbing composition comprising the benzilidene malonamide compound or a salt thereof as described in claim 1.

3. An external preparation comprising the benzilidene malonamide compound or a salt thereof as described in claim 1.

4. The external preparation of claim 3, further comprising inorganic powder.

* * * * *